United States Patent [19]

Mueller

[11] Patent Number: 4,702,809
[45] Date of Patent: Oct. 27, 1987

[54] PROCESS FOR THE PRODUCTION OF 1,2,3-TRICHLORO-2-METHYLPROPANE

[75] Inventor: Dieter J. Mueller, Marl, Fed. Rep. of Germany

[73] Assignee: Huels Aktiengesellschaft, Marl, German Democratic Rep.

[21] Appl. No.: 727,176

[22] Filed: Apr. 25, 1985

[30] Foreign Application Priority Data

Apr. 25, 1984 [DE] Fed. Rep. of Germany ....... 3415336

[51] Int. Cl.$^4$ .......................... B01J 1/10; C07C 17/06
[52] U.S. Cl. ........................... 204/157.63; 204/157.94
[58] Field of Search ....................... 204/157.63, 157.94

[56] References Cited

U.S. PATENT DOCUMENTS

| | | |
|---|---|---|
| 1,235,283 | 7/1917 | Brooks et al. . |
| 1,741,305 | 12/1929 | Jaeger . |
| 2,189,890 | 2/1940 | Engs . |
| 2,284,479 | 5/1942 | Rust et al. . |
| 2,302,228 | 11/1942 | Kharasch et al. . |
| 2,324,249 | 7/1943 | Vaughan et al. . |
| 2,380,500 | 7/1945 | Buc et al. . |
| 2,411,566 | 11/1946 | Evans . |
| 3,137,644 | 6/1964 | Bretschneider . |
| 3,405,046 | 10/1968 | Sennewald et al. . |
| 3,846,268 | 11/1974 | Zahalka et al. .............. 204/163 HE |

FOREIGN PATENT DOCUMENTS 106345  6/1974  German Democratic Rep. .

OTHER PUBLICATIONS

JACS 61:2145 (1939), 61:3433 (1939), 58:1028–1029 (1936), 69:2614–2616 (1947), 72:3577 (1950), 61:3432 (1939), 68, 787 (1946).
Brilshen E., III, 1, p. 320 (1958).
B. L. Chem. Soc., Japan 30 (1957), pp. 218–220.
Chem. Abs. 33:4190 (1939).

*Primary Examiner*—John F. Terapane
*Assistant Examiner*—Susan Wolffe
*Attorney, Agent, or Firm*—Millen & White

[57] ABSTRACT

For the production of 1,2,3-trichloro-2-methylpropane, 3-chloro-2-methylpropene is reacted with sulfuryl chloride in the presence of aldehydes and/or under the effect of light, especially UV light. The reaction is preferably performed in the liquid phase, especially at 30°–65° C. under normal pressure.

9 Claims, No Drawings

PROCESS FOR THE PRODUCTION OF 1,2,3-TRICHLORO-2-METHYLPROPANE

CROSS REFERENCE TO RELATED APPLICATIONS

This Application is related to commonly assigned U.S. Pat. No. 4,587,367 and Ser. Nos. 773,168 of and 695,107 of Jan. 25, 1985 644,418 and 644,466, both of Aug. 27, 1984, all of which disclosures are incorporated herein by reference.

BACKGROUND OF THE INVENTION

This invention relates to a process for the production of 1,2,3-trichloro-2-methylpropane by reacting 3-chloro-2-methylpropene with sulfuryl chloride in the presence of aldehydes and/or under the effect of light.

In a conventional addition reaction, the reaction of 3-chloro-2-methylpropene with sulfuryl chloride yields 1,2,3-trichloro-2-methylpropane with a boiling range of 159°–165° C. in a yield of 83% (J. Am. Chem. Soc. 68: 787 [1946]). In this reaction, 3-chloro-2-methylpropene is charged into a reactor, and the reaction is performed with heating by the gradual addition of a stoichiometric quantity of $SO_2Cl_2$ in total.

This reaction is unsatisfactory for an industrial process. On the one hand, the start of the reaction, after addition of a small amount of $SO_2Cl_2$, is delayed and must be initiated by gentle heating; on the other hand, there is the danger that the exothermic reaction, after startup, will proceed uncontrollably. Moreover, the yield and selectivity leave a lot to be desired.

The addition of chlorine to unsaturated olefinic compounds by means of sulfuryl chloride can, it is true, be accelerated by adding peroxide or radical-forming agents (J. Am. Chem. Soc. 61: 3 432 [1939]), but this method is used only in special cases. Normally, the same addition products are also readily obtainable using elemental chlorine. The yields, however, range only between 80% and 90%.

Other conventional reactions for the production of 1,2,3-trichloro-2-methylpropane, such as the direct chlorination of isobutane or isobutene, or the further chlorination of suitable $C_4$ chlorinated hydrocarbons such as, for example, 3-chloro-2-methylpropene, 1,3-dichloroisobutene, or 2-chloro-2-methylpropene proceed with even less selectivity. The end product of the process of this invention, 1,2,3-trichloro-2-methylpropene is useful for many purposes, e.g., as additional component for flame retardends or as a starting material for the preparation of the known compound cis- and trans-1-Chlor-2-methyl-propen-(1)-ol-(3), (Beilstein E III 1, p. 320) which is useful as derivating component for producing derivates of Cellulose and as pharmceuticals as described in C. A. 87 (1977) p. 579, 101874 q.

SUMMARY OF THE INVENTION

Accordingly, it is an object of this invention to provide a process permitting the production of 1,2,3-trichloro-2-methylpropane with high selectivity in a technically simple way.

Upon further study of the specification and appended claims, further objects and advantages of this invention will become apparent to those skilled in the art.

These objects have been attained according to this invention by reacting 3-chloro-2-methylpropene with sulfuryl chloride in the presence of aldehydes and/or under the influence of light, especially UV light, in accordance with the following equation, preferably in a temperature range from 30° to 65° C., especially in the liquid phase.

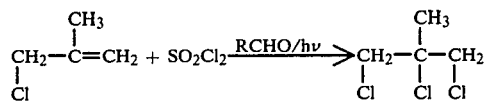

DETAILED DISCUSSION OF THE INVENTION

The selectivities of the manufacturing process according to this invention are at an unexpectedly high level, e.g., 91–98%. Chlorination reactions using sulfuryl chloride under the effect of light generally yield sulfonic acid chlorides as products in addition to chlorine substitution products. For this reason, chlorination reactions catalyzed by radical-forming agents are, in general, performed under exclusion of light (J. Am. Soc. 61: 2 142 [1939]). Thus, in particular, selective addition reactions using olefinic compounds and sulfuryl chloride under the effect of light have not been known.

It has now been found surprisingly that 3-chloro-2-methylpropene can be reacted in an addition reaction to form 1,2,3-trichloro-2-methylpropane with high selectivities of above 90% in the presence of aldehydes, or under the influence of light, or under the combined effect of aldehydes and light, using sulfuryl chloride.

It has been found that aldehydes and/or UV light regulate the course of reaction along the same lines in the direction toward addition, but that the respective selectivities and reaction velocities differ. The reaction actually takes place more rapidly under the effect of UV light but yields a somewhat lower selectivity as compared with the action of aldehydes. A mixed effect results under the combined action of aldehydes and UV light.

The sulfuryl chloride can be utilized in stoichiometric amounts, based on the amount of 3-chloro-2-methylpropene. It is preferably employed in less than stoichiometric quantities, e.g., 65–95% of the stoichiometric amount to facilitate reaction work-up.

Especially suitable aldehydes are the $C_4$-aldehydes. The use of other aldehydes is likewise possible, e.g., an aliphatic or olefinic aldehyde. Typically, suitable aldehydes will be those of $C_{2-10}$-alkyl groups or $C_{3-10}$-alkenyl groups. Isobutanal is an example. This aldehyde has the advantage of not being foreign to the system since it often initially will be present in trace amounts in the 3-chloro-2-methylpropene starting material as a result of preceding hydrolytic and/or oxidative processes. In general, the effect of atmospheric oxygen and/or water on 3-chloro-2-methylpropene exerted before and/or during the reaction does not present any problem since essentially non-interfering aldehydes are formed in such a case. Other suitable aldehydes are acrolein, crotonaldehyde, propionaldehyde, glycolaldehyde, benzaldehyde, etc.

It has been found that concentrations as low as 10–100 ppm of the aldehydes are catalytically active and enhance the reaction in the direction toward addition, i.e., increase the yield of desired product.

In general, concentrations of 10–10,000 ppm of the aldehydes are employed; preferably, about 100 ppm to 1,000 ppm of aldehyde is added, although higher concentrations of up to 10,000 ppm and more will be suitable. When an aldehyde is used, typical reaction temperatures are about 30°–65° C., reaction times are about 90–360 minutes and reaction pressures are 0.5–3 bar, preferably normal pressure. Using an aldehyde, yields are usually 92–98 mole %.

Especially suitable as the actinic radiation is light of a wavelength of 185–500 nm, preferably UV radiation of a wavelength of 200–400 nm. Intensities are not critical and sources are not critical as long as actinic radiation distributions (wavelength and/or intensity) are provided which achieve reaction results better than those of ambient conditions. Typically, radiation intensities of 15 W–10 kW or even more can be used, e.g., from conventional mercury lamps, e.g., Original Hanau Heraeus Lamps. Under the influence of radiation, typical reaction temperatures are 30°–65° C., reaction times 60–240 min and reaction pressures 0.5–3 bar, preferably normal pressure. Using light, yields are usually 90–96 mole %.

To the extent that the prior art reaction of 3-chloro-2-methylpropene may have been conducted in the presence of ambient radiation, this aspect, of course, is not part of this invention. This invention involves the conduction of the reaction under actinic radiation intensities greater than those of ambient conditions and distributions different from those of ambient conditions. The latter, of course, are meant to include radiation distributions normally existing in laboratories and/or plants where an intentional exposure to actinic radiation is not involved.

As can be seen from related application U.S. Pat. No. 4,587,367 the reason of this invention should be conducted in the essential absence of amines and phosphines described therein. These catalyze the reaction in the wrong direction. The amounts of amines and phosphines should be less than 10 ppm, preferably less than 1 ppm. See, U.S. Ser. No. 644,466. This may be of concern when the starting material may be contaminated with, e.g., an amine stabilizer. In this case, conventional means can be taken to lower the impurity content to the described levels.

The reaction can also be carried out both in the presence of light and in the presence of an aldehyde as the catalyst.

The process is suited for a discontinuous process, for example, in an agitated reactor, as well as for a continuous process, for example, in a tubular reactor or in a cascade. In a discontinuous mode of operation, 3-chloro-2-methylpropene is charged, preferably in a stoichiometric excess, into a heatable, coolable agitator-equipped reactor provided with a conventional light exposure device, reflux condenser, and feeding tube for sulfuryl chloride. The sulfuryl chloride is added in metered quantities in succession so that the heat produced in the exothermic reaction can be removed in a controlled fashion by way of the reflux condenser, and the reaction temperature is maintained in a range from about 30° to about 65° C. With satisfactory heat removal, the reaction time can be restricted to one hour or even less. It is also possible to conduct the reaction in solvents such as $CCl_4$ or other inert diluents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

An agitated apparatus with reflux condenser and dropping funnel with an immersed Hg high-pressure immersion lamp (15 W) is charged with 90.6 g of stabilizer-free 3-chloro-2-methylpropene (stabilizer content below 1 ppm), heated to 45° C., and within 30 minutes 108 g of $SO_2Cl_2$ is added in metered quantities with thermostat control of the agitated flask.

The gaseous $SO_2$ and, in some cases, HCl, released during the reaction under the effect of UV light, are withdrawn via the cooler. The reaction is stopped once the evolution of $SO_2$ has ceased. Thereafter the crude product is washed with water, the organic phase is dried over $K_2CO_3$ and subjected to analysis by gas chromatography to determine product composition. The result is listed in Table 1, line 1.

EXAMPLE 2

The process of Example 1 is followed, with the difference that (a) 1,000 ppm isobutyraldehyde and, respectively, (b) 1,000 ppm acrolein are added to the stabilizer-free 3-chloro-2-methylpropene, and the reaction is conducted without UV light under otherwise identical conditions. The result is indicated in Table 1, lines 2a and 2b.

EXAMPLE 3

The procedure of Example 1 is performed, except that 1,000 ppm isobutyraldehyde is added to the stabilizer-free 3-chloro-2-methylpropene and the reaction is conducted with UV light under otherwise identical conditions.

The result is set forth in Table 1, line 3.

COMPARATIVE EXAMPLE 4

The process is performed as set out in Example 1, but reacting 3-chloro-2-methylpropene without any additive with $SO_2Cl_2$ under exclusion of light.

The result is disclosed in Table 1, line 4.

TABLE 1

Reaction of Stabilizer-Free 3-Chloro-2-methylpropene with Sulfuryl Chloride Under the Effect of Aldehydes and/or UV Light

| Line | Reaction Under Effect of | Reaction Temp. °C. | Reaction Period Incl. Metering Time for $SO_2Cl_2$ Total Time Min | Metering Time min | Amount of Crude Product g | Composition of Pure Product %[+] 1,3-Dichloro-2-methyl propene | 3-Chloro-2-chloro-methyl-propene | 1,2,3-Tri-chloro-2-methyl-propane |
|---|---|---|---|---|---|---|---|---|
| 1 | UV Light | 45–50 | 100 | 30 | 146 | 2.5 | 3.5 | 92.0 |
| 2a | Isobutyraldehyde | 45–50 | 180 | 50 | 144 | 1.0 | 0.5 | 97.0 |
| 2b | Acrolein | 45–50 | 180 | 50 | 145 | 1.0 | 1.0 | 96.0 |

TABLE 1-continued

| | | | Reaction Period Incl. Metering Time for $SO_2Cl_2$ | | | Composition of Pure Product %[+] | | |
|---|---|---|---|---|---|---|---|---|
| Line | Reaction Under Effect of | Reaction Temp. °C. | Total Time Min | Metering Time min | Amount of Crude Product g | 1,3-Dichloro-2-methyl propene | 3-Chloro-2-chloro-methyl-propene | 1,2,3-Tri-chloro-2-methyl-propane |
| 3 | UV Light/ Isobutyraldehyde | 45–50 | 130 | 30 | 146 | 1.5 | 1.5 | 95.0 |
| 4 | Comparative Experiment | 45–50 | 130 | 30 | 133 | 8.5 | 8.5 | 82.0 |

[+]Remainder up to 100% not identified in detail.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of 1,2,3-trichloro-2-methylpropane with selectivity substantially higher than that achieved when the same reaction is conducted in the presence of ambient light comprising reacting 3-chloro-2-methylpropene with sulfuryl chloride essentially in the absence of amines and phosphines under the effect of actinic radiation having a spectral distribution containing actinic wavelength intensities greater than those present under ambient condition.

2. A process according to claim 1, wherein the radiation is UV light.

3. A process of claim 1, wherein the radiation is of a wavelength of 185–500 nm.

4. A process of claim 1, wherein the radiation is of a wavelength of 200–400 nm.

5. A process of claim 1, wherein the actinic radiation impinging on the reaction is derived from a high intensity UV light source.

6. A process of claim 1, also carried out in the presence of a catalytic amount of an aldehyde effective for catalyzing said reaction.

7. A process of claim 1, wherein the reaction is performed in the liquid phase.

8. A process of claim 1, wherein the reaction is performed at 30°–65° C. under normal pressure.

9. A process of claim 1, wherein sulfuryl chloride is used in less than a stoichiometric amount, based on the amount of 3-chloro-2-methylpropene.

* * * * *